United States Patent [19]

Frazzini et al.

[11] 4,244,800

[45] Jan. 13, 1981

[54] APPARATUS FOR USE IN RAPID AND ACCURATE CONTROLLED-POTENTIAL COULOMETRIC ANALYSIS

[75] Inventors: Thomas L. Frazzini, Frankfort; Michael K. Holland, LaGrange Park; Charles E. Pietri; Jon R. Weiss, both of Downers Grove, all of Ill.

[73] Assignee: The United States of America as represented by the United States Department of Energy, Washington, D.C.

[21] Appl. No.: 69,152

[22] Filed: Aug. 23, 1979

[51] Int. Cl.³ .................................. G01N 27/46
[52] U.S. Cl. ............................. 204/195 R; 204/1 T; 204/195 T
[58] Field of Search ................ 204/1 T, 195 R, 1 M, 204/195 T

[56] References Cited

U.S. PATENT DOCUMENTS

| | | | |
|---|---|---|---|
| 3,498,888 | 3/1970 | Johansson | 204/195 T |
| 4,003,705 | 1/1977 | Buzza et al. | 204/195 T |

OTHER PUBLICATIONS

Brown, "J. Phys. E." (GB), vol. 5, No. 4, (Apr. 1972), pp. 365–368.
Karlsson et al, "Talanta", vol. 18, pp. 459–465, No. 5 (1971).
Holland et al, "Analytical Chemistry", vol. 50, pp. 236–240 (1978).

*Primary Examiner*—T. Tung
*Attorney, Agent, or Firm*—James E. Denny; Frank H. Jackson; Donald P. Reynolds

[57] ABSTRACT

An apparatus for controlled-potential coulometric analysis of a solution includes a cell to contain the solution to be analyzed and a plurality of electrodes to contact the solution in the cell. Means are provided to stir the solution and to control the atmosphere above it. A potentiostat connected to the electrodes controls potential differences among the electrodes. An electronic circuit connected to the potentiostat provides analog-to-digital conversion and displays a precise count of charge transfer during a desired chemical process. This count provides a measure of the amount of an unknown substance in the solution.

10 Claims, 4 Drawing Figures

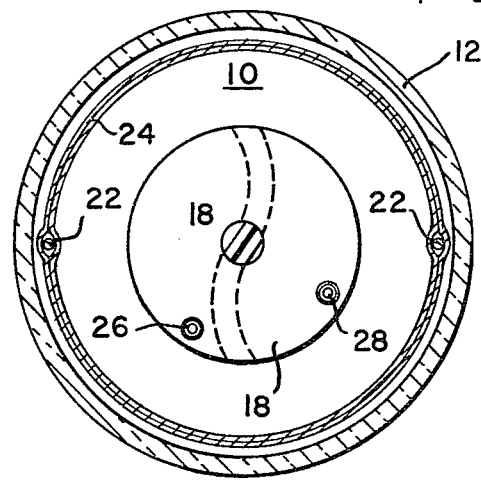
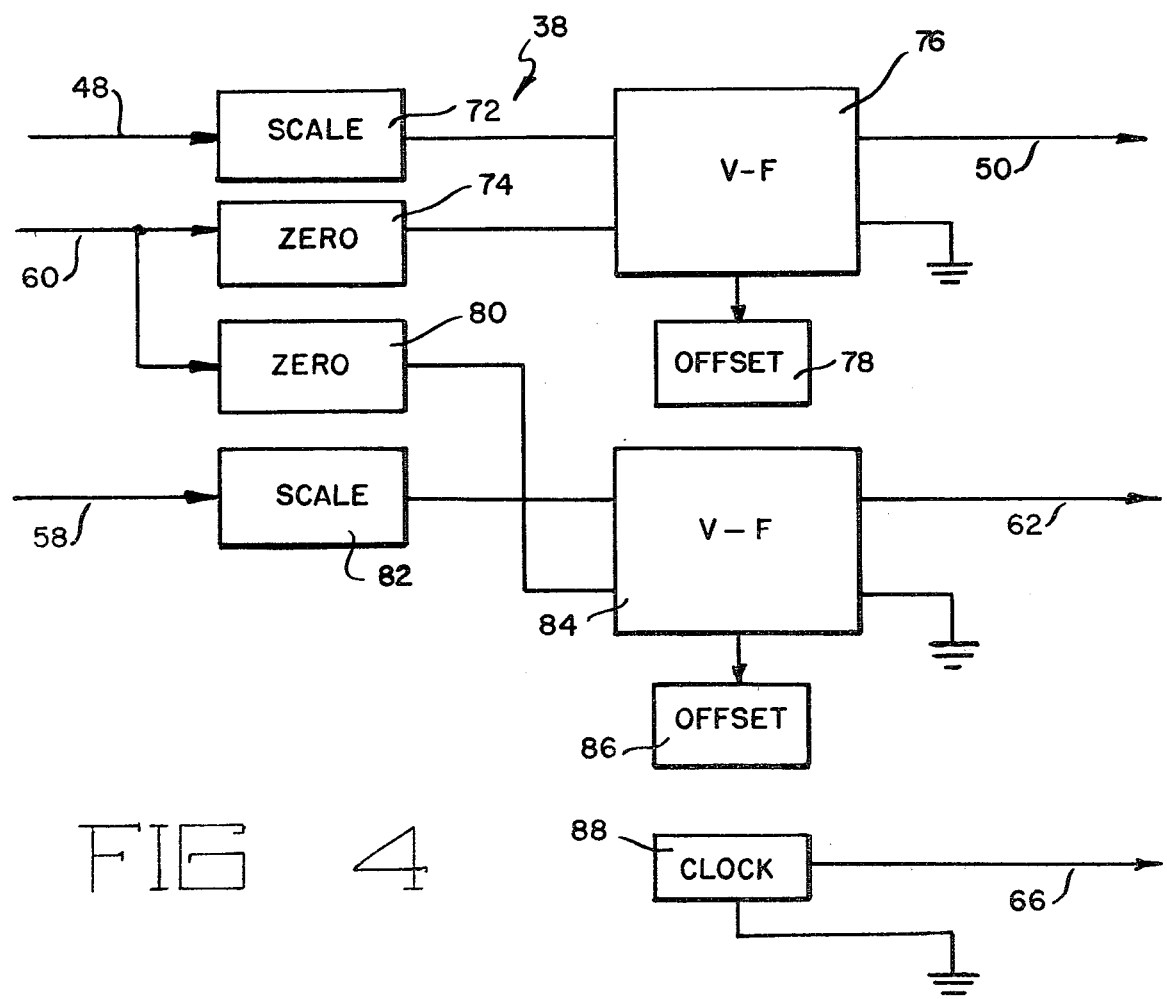

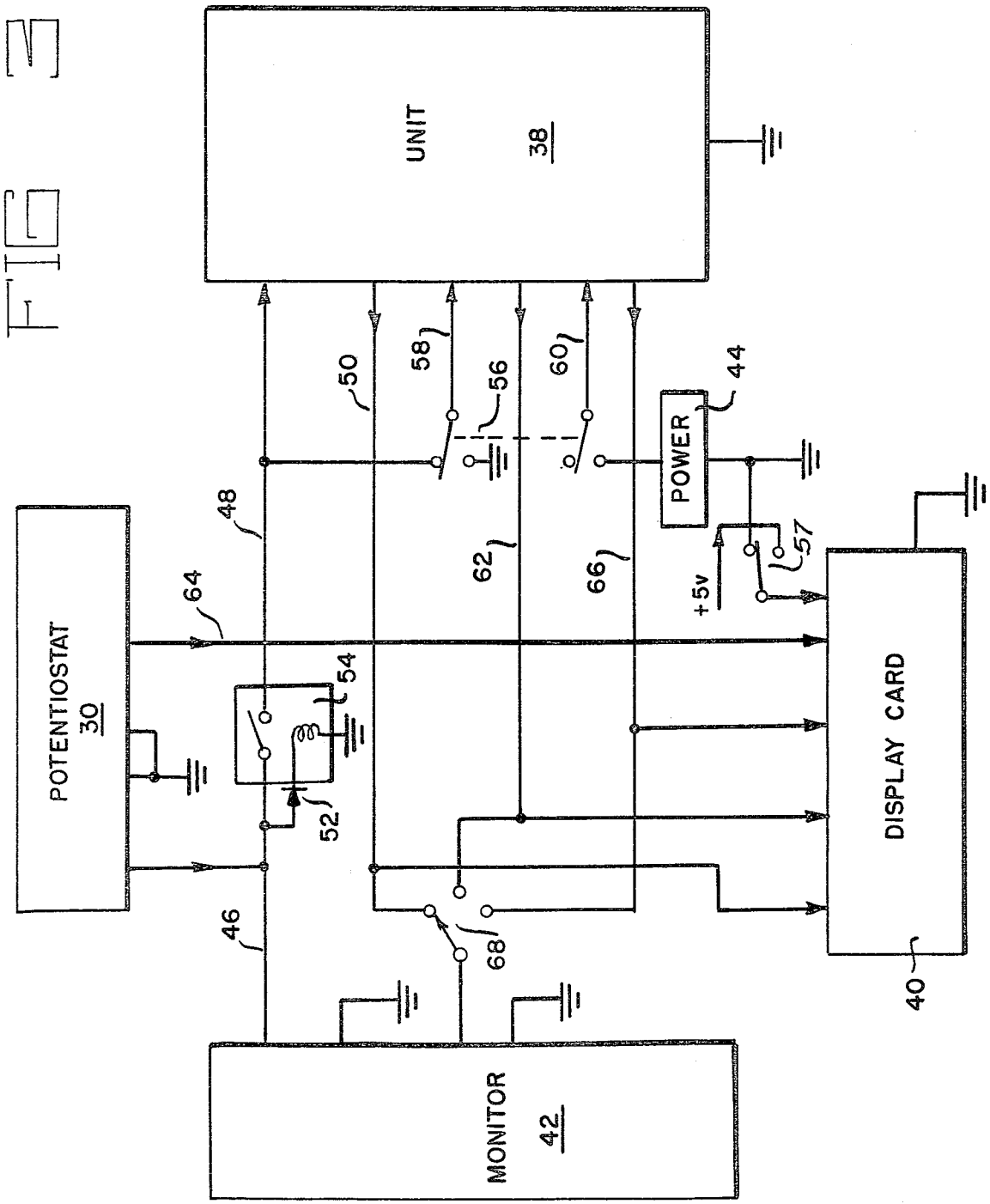

APPARATUS FOR USE IN RAPID AND ACCURATE CONTROLLED-POTENTIAL COULOMETRIC ANALYSIS

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to the measurement of quantities of an electroactive species in solution by controlled-potential (C.P.) coulometric analysis.

C.P. coulometry is a method of measuring the quantity of a particular electroactive species in a solution by carrying out an electrochemical reaction involving the electroactive species to be measured. An electroactive species is defined as a species that will undergo a chemical reaction in solution at the surface of an electrode in response to an applied voltage. The reaction chosen must involve the passage of an electric current and knowledge of the oxidation states of the reactants. The amount of current that flows while the reaction proceeds to a determinable fraction of completion provides a measure of the quantity of the substance in solution. This method is well known. It is normally carried out using a C.P. coulometer which is a device for controlling the potential of a working electrode to a selected potential with respect to a reference electrode by applying enough voltage and passing enough current between the working electrode and a counter electrode to cause this selected potential to be maintained. The value of the control potential is selected to favor the particular reaction that is desired and thus to discriminate against unwanted reactions. The coulometer has an integrator module which integrates the current passing between the working and counter electrodes. The integrated current is directly proportional to the amount of electroactive species electrolyzed. When the desired reaction is allowed to go to an exactly known fraction of completion, the number of electron units of charge divided by the fraction electrolyzed and divided by the number of electrons involved in each electrochemical reaction that takes place is equal to the number of molecules of the test substance in the solution.

Two problems generally arise in the making of precise and accurate measurements by C.P. coulometry. The first is the fact that to permit the reaction to proceed substantially to completion often takes an appreciable amount of time. This is especially of concern when many samples are to be analyzed. The time also leads to a second problem in that the longer the time for analysis, the greater is the chance for changes in parameters such as voltage or temperature that may produce error in the readings. One alternative that has been applied to increase the speed of obtaining results in coulometry is to use one of several methods for predicting the end point of the reaction. If this is done without a computer, however, the time saved is taken up in calculation and the cost of using a computer for such predictive end-point analysis is sufficiently high that it is desirable to look for different methods. One such alternative is referred to as an empirical end-point method. This refers to a technique in which the analysis is terminated at what is believed to be a predetermined fraction of the final value. Various methods of stirring the solution of facilitate reaction have also reduced the time for analysis. However, all of the methods of coulometry previously used in which the reaction is not carried to completion have possibilities for error that are intolerable for highly accurate quantitative measurement of substances such as plutonium in solution. Such measurements must be made with acceptable speed and to high accuracy and precision.

It is an object of the present invention to provide a better apparatus for controlled-potential coulometric analysis.

It is a further object of the present invention to provide for controlled-potential coulometric analysis a digital integrator that gives minimal change in net output with changes in temperature of the operating environment, and is stable electronically in use over long periods of time.

It is a further object of the present invention to provide an apparatus for controlled-potential coulometric analysis including a digital integrator that is not subject to the systematic errors found in state-of-the-art analog integrators caused by capacitor leakage, capacitor dielectric absorption, amplifier drift, and amplifier offset.

It is a further object of the present invention to provide for controlled-potential coulometric analysis an integrator that can be calibrated accurately in a straight-forward manner by electrical means to relate chemical equivalents to the electrochemical constant, the faraday.

It is a further object of the present invention to provide an apparatus for controlled-potential coulometric analysis that gives rapid, highly precise and highly accurate results.

It is a further object of the present invention to provide a digital integrator compatable with automation of controlled-potential coulometry.

Other objects will become apparent in the course of the detailed description of the invention.

SUMMARY OF THE INVENTION

An apparatus for fast, precise controlled-potential coulometric analysis of an electroactive species in a solution includes a cell containing the solution, a set of electrodes in the solution, and a potentiostat connected to the electrodes. Outputs from the potentiostat are taken to an electronic circuit that provides a visual digital indication of the current flow in the solution during analysis. The circuit includes means for controlling and monitoring operation and provides information that leads to a precise determination of the amount of the electroactive species.

BRIEF DESCRIPTION OF THE DRAWINGS

FIG. 2 is a sectional end view of the cell of FIG. 1, taken along section lines 2—2.

FIG. 3 is a partial block diagram of an electronic circuit for controlling the apparatus of FIG. 1.

FIG. 4 is a detailed block diagram of the converter of FIG. 3.

DETAILED DESCRIPTION OF THE INVENTION

Figure 1:
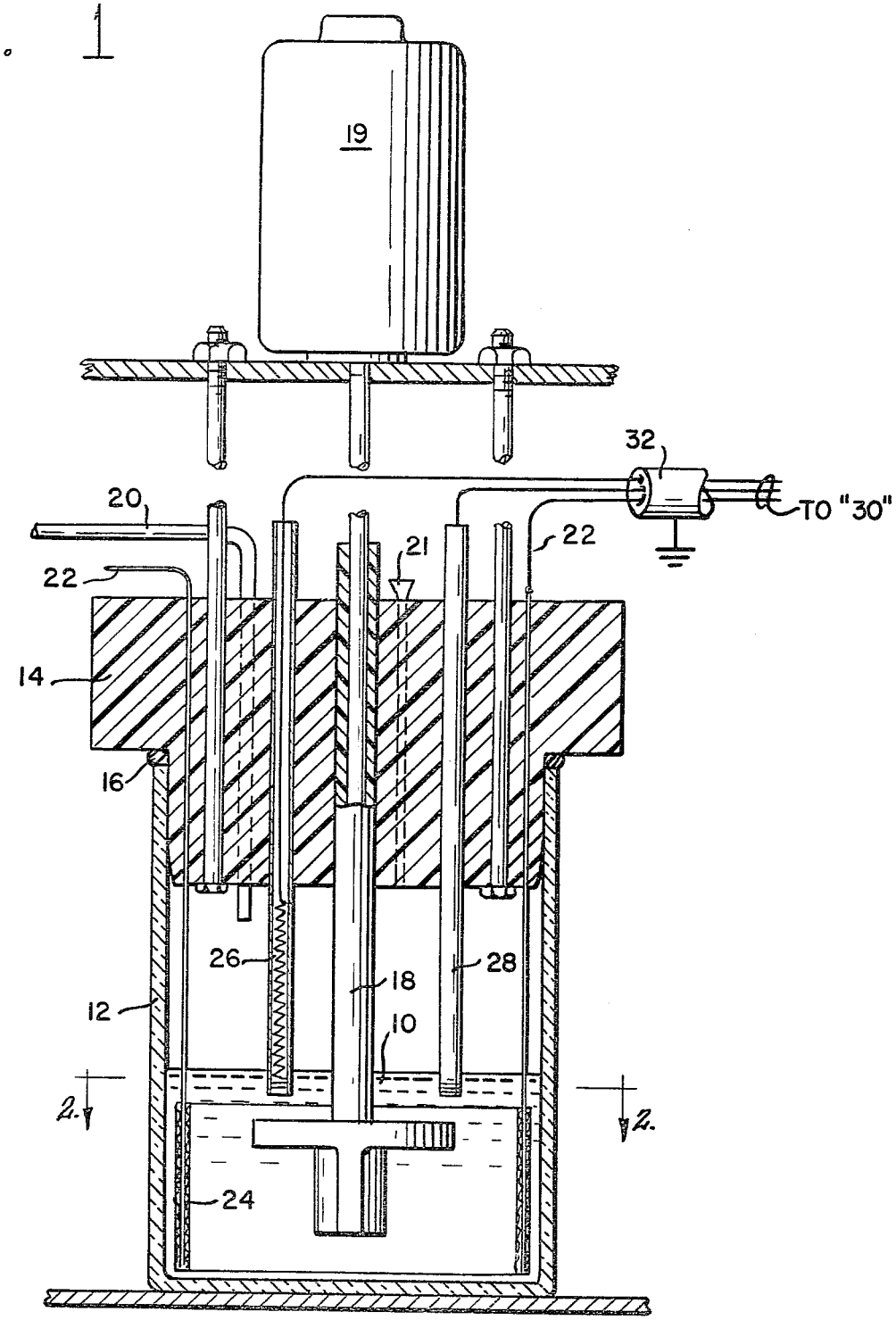
FIG. 1 is a partial sectional side view of an apparatus for C.P. coulometric analysis.

FIG. 1 is a partial sectional side view of an apparatus for effecting controlled-potential coulometric analysis. In FIG. 1 a solution 10 including as a solute the reactant to be measured is contained in a cell 12. A cell head 14 is placed on cell 12 and an airtight seal is maintained by O-ring 16. Cell head 14 has openings for a stirrer 18, driven by motor 19, a gas line 20 and a vent 21 for maintaining a desired atmosphere of argon or the like over the surface of solution 10 and a feedthrough 22 to make an electrical connection with a working electrode 24. Working electrode 24 is typically made of a metal mesh for increasing the surface area that is in contact with solution 10. A counter electrode 26 and a reference electrode 28 are also brought through cell head 14 and placed in electrical contact with solution 10. It is convenient although not necessary to support counter electrode 26 and reference electrode 28 by their placement in cell head 14. The connections of working electrode 24, counter electrode 26 and reference electrode 28 to potentiostat 30 are best protected by connecting them through a twisted shielded triaxial cable 32 to potentiostat 30.

An apparatus of the general type of FIG. 1 is well known and has been used for some years to effect coulometric analysis. This is done by placing a sample of the quantity to be electrolyzed in solution 10 and controlling the potential difference between the working electrode 24 and reference electrode 28 to a selected value by applying a voltage between the counter electrode 26 and the working electrode 24. This permits a desired reaction to proceed and does not allow certain other reactions to occur. From a measurement of the flow of current between counter electrode 26 and working electrode 24 the quanity of sample can be calculated. The integral of that current with respect to time represents the charge transferred in accomplishing the desired chemical reaction and it is a measure of the number of molecules which has undergone the reaction. While controlled-potential coulometric analysis is applicable to the measurement of a number of substances, it will be illustrated here with reference to a particular reaction of interest, the oxidation of plutonium in the 3+ oxidation state to the 4+ oxidation state. This is accomplished by first assuring that essentially all plutonium in the solution has been reduced to the 3+ oxidation state. That state is achieved by establishing the potential such that electrochemical reduction occurs. The current need not be monitored during reduction since the only measured current of interest will be that flowing during oxidation. During oxidation the potential is controlled at a value approximately 0.18 V above the formal potential $E^o$, and the oxidation is to the desired degree of completion when the current reaches the constant value of the background current. This process represents an application of the Nernst equation which is $$E - E^{o'} = \frac{RT}{nF} \ln \frac{ox}{red} \qquad (1)$$

The Nernst equation may be solved for the ratio ox/red as follows:

$$\frac{ox}{red} = e^{\frac{E-E^{o'}}{k}} \qquad (2)$$

In these equations E is the solution redox potential, $E^o$, is the formal potential, k is the logarithm coefficient RT/nF which, for a one-electron reaction at 25° C. or 298K is equal to 0.0256924 V, ox is the fraction in the oxidized state, and red is the fraction in the reduced state. Since red equals 1-ox, the preceding equation can be solved to give $$ox = \frac{e^{\frac{E-E^{o'}}{k}}}{1 + e^{\frac{E-E^{o'}}{k}}} \qquad (3)$$

and $$red = 1 - \frac{e^{\frac{E-E^{o'}}{k}}}{1 + e^{\frac{E-E^{o'}}{k}}} \qquad (4)$$

By substituting the solution redox potential after reduction, $S_{red}$, for E in equation 3 (since the fraction not reduced is in the oxidized state) and the solution redox potential after oxidation, $S_{ox}$, for E in Equation 4, the sum of ox and red is equal to the fraction of the total plutonium which was not electrolyzed for the given $S_{red}$ and $S_{ox}$ pair. Subtraction of the fraction not electrolyzed from unity yields the correction factor, f, i.e. the fraction of the plutonium electrolyzed, which simplifies to:

$$F = \frac{e^{\frac{S_{ox}-E^{o'}}{k}}}{1 + e^{\frac{S_{ox}-E^{o'}}{k}}} - \frac{e^{\frac{S_{red}-E^{o'}}{k}}}{1 + e^{\frac{S_{red}-E^{o'}}{k}}} \qquad (5)$$

The equation for f thus allows the calculation of the fractional part of the quantity of a reactant in a solution that is electrolyzed between the reduction and oxidation potentials. That result is unaffected if the electrolyzing potential is increased at the beginning of the reaction to a value sufficient to speed the reaction but not to such a high value as to cause interfering reactions.

It can be seen from the preceding mathematical expressions that three things must be determined to measure the quantity of a substance such as plutonium by oxidizing to a fraction of completion in the apparatus of FIG. 1. These are the solution redox potential after reduction, $S_{red}$, the solution redox potential after oxidation, $S_{ox}$, and the quantity of charge transferred during oxidation. This assumes that the formal potential $E^o$, is known for the reaction, which is normally the case. The redox potential after reduction and that after oxidation are quantities which can be measured at a single appropriate time for each. It is thus relatively easy to achieve almost any desired degree of accuracy within instrumental capability in making those measurements and hence to achieve a comparable degree of accuracy in the determination of the fraction of reactant that is oxidized in the time that is taken to make a measurement. However, the measurement of the charge transferred while the measurement is being made represents a time integral over the entire span of the measurement and it is this quantity that is the most prone to error as a result of any changes that take place while the measurement is being made. An electric circuit for making such measurement is shown in FIGS. 3 and 4. FIG. 3 is an overall block diagram of the circuit that is connected to the output terminals of a potentiostat 30 as indicated in FIG. 1, and FIG. 4 is an expanded view of the circuit elements of converter 38 of FIG. 3. In FIGS. 3 and 4 potentiostat 30 is a wellknown electrical device for applying a controlled potential difference to electrodes in a solution for coulometric determination. A potentiostat normally has internal means by which an operator can vary the potential to select and drive a particular reaction and its output is a signal that is proportional to the current flow between two electrodes in the solution. A potentiostat normally has available an enabling signal to signify the beginning of a measurement. In FIGS. 3 and 4 the major components shown are the converter unit 38, a display card 40, a monitor 42 and a power supply 44. Line 46 is the output terminal from potentiostat 30 that carries a voltage proportional to current flow in a working electrode. This voltage is the readout signal. Line 46 is connected to monitor 42 to provide means for observing the progress of a reaction and it is connected to line 48 through relay 54. Line 46 is also used to supply an alignment signal from monitor 42. An amplifier/comparator 52 causes relay 54 to close and connect line 46 to line 48 only when the voltage is in a desired polarity which here is negative. The amplifier/comparator 52 is shown symbolically as a diode, but will preferably be a commercially obtained module. Some such means of protecting converter 38 against positive potentials is desirable because of phases of operation of potentiostat 30 that will be described later. The signal entering converter 38 on line 48 is normally the read-out signal from potentiostat 30. After processing in the converter 38, the read-out signal, now a digital signal, leaves converter 38 on line 50 from which it is fed to display card 40 which counts it and displays the count as a number proportional to the quantity of reactants which has been electrolyzed. The signal on line 50 may also be selected by switch 68 for connection to monitor 42 for purposes of operational control, alignment, and troubleshooting.

Switch 56 is a double-pole double-throw switch that is shown in a test position in which the signal on line 48 is connected to line 58 which supplies a zero input signal to converter 38. In the test position the same signal is applied as a readout signal on line 48 and also as a zero input signal on line 58 to permit alignment of unit 38. In the normal operating position line 458 is grounded or left open and thus the zero input, line 58, receives no signal. Switch 56 also connects power from an adjustable power supply 44 to line 60 in normal operating position. Line 60 supplies an offset signal to unit 38.

The outputs from converter 38 are on three lines. The first of these, line 50, carries the digital read-out signal which is the signal of principal interest. This is connected through switch 68 to monitor 42 for observation and troubleshooting and it is also connected to display card 40 where it is counted to provide a visual indication of the amount of charge transfer which is proportional to the quantity of the desired reactant in solution. A zero output signal leaves converter 38 on line 62 and is similarly available to monitor 42 through the rotary switch 68. Line 62 is also connected to display card 40 where it is counted to display the zero signal level. The third output from converter 38 is a clock signal on line 66 which is similarly connected through rotary switch 68 to monitor 42 and is connected to display card 40 where it is counted to display the clock signal. Line 64 carries a signal to clear and enable counters and visual displays in display card 40. Switch 57 is operable to connect a hold signal to display card 40 to freeze the visual displays for observation while counters continue to count.

A view in more detail of converter 38 is shown in FIG. 4 in which the corresponding input and output line have the same numbers as in FIG. 3. In FIG. 4 the readout signal that enters converter 38 on line 48 is connected through a scaler 72 to a voltage-to-frequency converter 76. The scaler 72 is an adjustment, typically a potentiometer, to set converter 76 to a desired value of full-scale reading for a predetermined value of input voltage on line 48. An offset signal enters zero adjust unit 74 from line 60 and is then coupled as a second input to voltage-to-frequency converter 76. Offset gain adjust unit 78 controls the zero setting of voltage-to-frequency unit 76 to a desired value to correspond to a given offset signal. The result is to generate an output signal on line 50 that is proportional to the algebraic sum of the input signals to voltage-to-frequency converter 76 that enter from scaler 72 and zero adjust unit 74. The offset signal that enters unit 38 on line 60 is also made subject to an adjustable scale setting in zero adjust unit 80 and is connected as one input to voltage-to-frequency converter 84. A zero input signal received on line 58 is applied to the adjustable scale unit 82 to cause voltage-to-frequency converter 84 to generate a signal whose frequency is proportional to the zero setting. Offset adjust 86 is a controller of the proportionality of voltage to frequency in voltage-to-frequency unit 84. Units 74, 78, 80, and 82 and offset adjust 86 are typically potentiometers. The result of the controls and adjustments in an output on line 62 that is proportional to the algebraic sum of the zero input signal on line 58 as scaled and the offset signal on line 60, also as scaled. The third output signal from unit 38 is a fixed frequency outpu at one kilohertz from clock 88 that is delivered to line 66. The clock is normally used only in the alignment procedure, since elapsed measurement time need not be known to the millisecond.

The present invention provides a fast and accurate measurement of the quantity of a particular reactant by coulometric analysis. This is of particular interest in an automated measuring apparatus in which a substantial plurality of the cells 12 of FIG. 1 is supplied in a controlled time sequence for measurement. In such a case it would be most useful to have several sets of the apparatus of FIG. 1 connected to a potentiostat such as potentiostat 30 but without the balance of the equipment of FIGS. 3 and 4. This would enable the application of current to the solution 10 in cell 12 so as to reduce all of the reactants in solution 10 to the desired oxidation state before measurement. In case of measurements of plutonium, for example, this would involve a preliminary reduction to the $+3$ oxidation state of plutonium. The current taken to reach the reduction state need not be measured and the reduction can therefore be done with a conventional potentiostat or the equivalent on a particular cell 12 that is not connected to the measuring apparatus of the present invention. Following the preliminary reduction the fast and accurate determination of the quantity of the desired reactant is made by indexing the cell 12 into a position for connection to the balance of the apparatus of the invention. The measuring cycle is started by measuring the reduction potential, then taking the solution redox potential to the highest value with respect to the potential of the reference electrode 28 in FIG. 1 that will permit the desired reaction without producing unwanted reactions. In the case of coulometric determination of plutonium from the $+3$ oxidation state to the $+4$ oxidation state, the redox potential at the start of the reaction is typically between 0.45 Volts and 0.52 Volts. If the reaction is initiated with the working electrode 24 set at a potential of 0.92

Volts with respect to the reference 28, no unwanted reactions will be favored and the reaction rate will be accelerated. The best operation has been observed to take place with the control potential starting at 0.92 Volts and being held there until the exponential decay of the current has decreased to 100 μA. The control potential can be decreased until background current is obtained (about 1 μA). At this point the measured solution redox potential will equal the control potential and will be at a value between 0.83 and 0.85 Volts with respect to the potential on the reference electrode 28 of FIG. 1. The fraction of completion F can now be calculated from Equation 5 from the measured values of $S_{ox}$, $S_{red}$, and $E^{o'}$, the formal potential. The quantity $E^{o'}$ can be determined after completion of a given analysis by repeating the reduction of the sample, then oxidizing to half the counted value of charge. The measured value of the redox potential at this point is $E^{o'}$. This is typically done once a day unless there is a change in reactants, either deliberately or through contamination.

Measurement of the net charge that has flowed during oxidation, divided by F, divided by the number of state changes (here 1) provides an accurate and fast measurement of the quantity of plutonium that has been oxidized. If it is desired to make C.P. coulometric measurements of electronegative species, the comparator 52 will be adjusted or replaced to operate with relay 54 to pass signals of the proper potential. Input connections to voltage-to-frequency converters 76 and 84 will be reversed to count upon the opposite polarity.

An apparatus for the practice of the present invention has been built and used at the New Brunswick Laboratory of the United States Department of Energy for the analysis of plutonium. The potentiostat 30 was part of a Controlled-Potential Coulometer System, Model 3, manufactured by M-T Electronics Company. Amplifier/comparator 52 was a differential comparator, Model TI 72710, manufactured by Texas Instruments Company. The voltage-to-frequency converters 76 and 84 were Analog Devices, Model 458L. Clock 88 was a Vectron Crystal Oscillator, Model CO-235T. Scaler adjusts 72 and 82, zero adjusts 74 and 80, and offset adjusts 78 and 86 were all potentiometers. Using this apparatus, it was possible to measure plutonium content with a reliability of 0.02% relative standard deviations in an oxidation time of five minutes.

The embodiments of the invention in which an exclusive property or privilege is claimed are defined as follows:

1. In an apparatus for controlled-potential coulometric analysis of an electroactive species in a solution, including a cell containing the solution, means for supplying a controlled atmosphere in the cell, means for stirring the solution in the cell, a working electrode disposed in the cell in electrical contact with the solution, a counter electrode disposed in the cell in electrical contact with the solution, a reference electrode disposed in the cell in electrical contact with the solution, a potentiostat connected to the working electrode, the counter electrode and the reference electrode for applying controlled electrical potential differences between the working electrode and the reference electrode and between the counter electrode and working electrode, an improved means for obtaining a digital electrical equivalent to electric current flow through the solution, the improvement comprising:

a first scaler connected to an output of the potentiostat and receiving an electrical signal from the potentiostat that is proportional to current through the working electrode;

a first voltage-to-frequency converter connected to the first scaler and receiving as an input a scaled signal from the first scaler, and producing a digital readout signal;

a first zero adjust connectable to a power supply and to the first voltage-to-frequency converter to provide a scaled zero input signal to the first voltage-to-frequency converter;

a second voltage-to-frequency converter;

a second zero adjust connectable to a power supply and connected to provide a zero input to the second voltage-to-frequency converter;

a second scaler connectable to the readout signal and to electrical ground and connected to the second voltage-to-frequency converter to produce a digital zero-output signal;

a clock producing an electrical signal at a fixed frequency; and a display card connected to the means for obtaining and displaying visually a count that is proportional to a current flow through the solution.

2. The apparatus of claim 1 wherein said display card is connected to provide a visual digital indication of the digital readout signal, the digital zero output signal and the clock signal.

3. The apparatus of claim 2 comprising in addition means connectable electrically to the potentiostat to produce alignment signals.

4. The apparatus of claim 3 comprising in addition means for resetting the display card to begin a measurement.

5. In an apparatus for controlled-potential coulometry in which an electrostatic species is disposed in a cell containing electrodes and in which a voltage control means is connected to the electrodes to apply to them controlled voltages, an improved converter means connected to the voltage control means for converting a voltage proportional to current flow in the cell to a digital signal, the improvement comprising:

a first integrator means having first and second input means, means for adding signals received by said first and said second input means, said first input means receiving an electrical signal from said voltage control means that is proportional to current flow in the cell, said second input means receiving a predetermined offset signal, a second integrator means connected to said offset signal producing a digital readout signal; and a display card connected to said first and second second integrator means for displaying a count proportional to current flow in the cell.

6. The apparatus of claim 5 wherein said voltage control means comprises a potentiostat.

7. The apparatus of claim 5 wherein said first integretor means comprises a first voltage-to-frequency converter.

8. The apparatus of claim 7 wherein said first voltage-to-frequency converter has a voltage input and a current input.

9. The apparatus of claim 7 wherein said second integrator means comprises a second voltage-to-frequency converter.

10. The apparatus of claim 9 wherein said second voltage-to-frequency converter has first and second inputs, said first input connected to said offset signal, and said second input selectively receiving an alignment signal.

* * * * *